(12) United States Patent
Momeni et al.

(10) Patent No.: US 7,632,249 B2
(45) Date of Patent: Dec. 15, 2009

(54) SYRINGE ASSIST FOR INFUSION PUMP

(75) Inventors: Ahmad Momeni, Mission Viejo, CA (US); Charles Grey, Irvine, CA (US)

(73) Assignee: Curlin Medical Inc., East Aurora, NY (US)

( * ) Notice: Subject to any disclaimer, the term of this patent is extended or adjusted under 35 U.S.C. 154(b) by 729 days.

(21) Appl. No.: 11/262,258

(22) Filed: Oct. 28, 2005

(65) Prior Publication Data

US 2008/0021396 A1    Jan. 24, 2008

(51) Int. Cl.
     *A61M 37/00*    (2006.01)
     *A61M 1/00*    (2006.01)
     *A61M 5/20*    (2006.01)

(52) U.S. Cl. .................... 604/154; 604/151; 604/134

(58) Field of Classification Search .......... 604/134, 604/151, 154
See application file for complete search history.

(56) References Cited

U.S. PATENT DOCUMENTS

| | | | |
|---|---|---|---|
| 2,877,714 A | | 3/1959 | Sorg et al. |
| 5,085,643 A | | 2/1992 | Larkin et al. |
| 5,545,140 A | | 8/1996 | Conero et al. |
| 5,575,631 A | | 11/1996 | Jester |
| 5,683,233 A | | 11/1997 | Moubayed et al. |
| 5,722,956 A | * | 3/1998 | Sims et al. .................. 604/131 |
| 5,791,881 A | | 8/1998 | Moubayed et al. |
| D408,911 S | | 4/1999 | Moubayed et al. |
| 5,924,852 A | | 7/1999 | Moubayed et al. |
| 5,944,693 A | * | 8/1999 | Jacobs ......................... 604/134 |
| 6,164,921 A | | 12/2000 | Moubayed et al. |
| 6,371,732 B1 | | 4/2002 | Moubayed et al. |
| 6,428,509 B1 | * | 8/2002 | Fielder ........................ 604/154 |
| 6,551,277 B1 | | 4/2003 | Ford |
| 2003/0233071 A1 | * | 12/2003 | Gillespie et al. ............. 604/151 |
| 2004/0019607 A1 | | 1/2004 | Moubayed et al. |
| 2004/0064435 A1 | | 4/2004 | Moubayed et al. |
| 2008/0221496 A1 | * | 9/2008 | Baraldi ........................ 604/4.01 |

* cited by examiner

*Primary Examiner*—Nicholas D Lucchesi
*Assistant Examiner*—Rebecca E Eisenberg
(74) *Attorney, Agent, or Firm*—Hodgson Russ LLP (57) ABSTRACT

A syringe assist device for preventing vacuum stall in an infusion pump which extracts fluid medication from a conventional syringe. The device is a plunger housed within a front case and a back case. The plunger is comprised of a cocker, a cradle, and a base member. The cocker and cradle are compressively retained by a spring spanning therebetween. The cocker includes a locking member which cooperates with a wedge type locking member defined by the back case to prevent movement along the base member. The cradle includes a syringe barrel compression member. In its unlocked position, the cocker and the cradle slide against the base member in unison, while in its locked position, only the cradle slides against the base member, thereby enabling a unidirectional compressive force upon the syringe. By this compressive force, the vacuum created within the syringe during infusion is eliminated, thereby eliminating vacuum stall.

18 Claims, 6 Drawing Sheets

SYRINGE ASSIST FOR INFUSION PUMP

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

This invention generally relates to infusion pump systems. More particularly, this invention relates to infusion pump systems having vacuum assist mechanisms for preventing vacuum stall during infusion.

2. Description of the Related Art

Means for supplying patients with fluid medication for sustained periods in a controlled manner is well known in the art. One such commonly known and well recognized means is a bag filled with fluid medication which was fed into the patient by gravitational force through intravenous tubing having drip or other controllers. More specifically, a sterile container such as a glass or plastic bottle, or a plastic bag was attached to one end of a drip chamber, and the other end of the same was attached to a tube. The drip chamber allowed the fluid to flow one drop at a time, and the tube had an attached hollow needle that was inserted into the vein. Further connectors could be attached to the tube, which permitted other fluid medication to be delivered through the same needle. The adjustability of the flow rate in such prior devices was quite limited, however, and a variety of expensive and complicated flow control valves and devices have been developed. Where fluctuations in the flow rate were not critical, the aforementioned gravity drip system continues to be used for its utter simplicity.

In an attempt to obtain even greater control over the flow rate, peristaltic and other electrically driven pumps were developed. Conventional peristaltic pumps typically have a section of resilient tubing positioned between a wall and a set of rollers or reciprocating pushers that progressively compress sections of tubing to facilitate the pumping of a liquid therethrough. Such peristaltic pumps known in the art include teachings from U.S. Pat. No. 2,877,714 to Sorg, et al. Improvements thereto have also been made, such as those teachings of a curvilinear peristaltic pump in U.S. Pat. No. 6,371,732 to Moubayed, et al., which is wholly incorporated by reference herein.

In many situations, the aforementioned elastic bags filled with fluid medication were used with peristaltic pumps. However, there were other instances where a syringe containing fluid medication was preferable, referred to in the art as "IV push." As will be appreciated by a person of ordinary skill, the use of peristaltic pumps for IV push caused a peculiar situation known as vacuum stall. As the fluid medication was extracted from the syringe, a vacuum was created therein by the pressure difference between the inside and the outside of the syringe. Essentially, as the amount of fluid was decreased inside the syringe, the space occupied by that fluid was decreased at a reduced rate, creating a vacuum. With more fluid being extracted from the syringe, the force required to extract the same became greater, eventually reaching a point where the peristaltic pump could not overcome the vacuum force. Upon reaching this point, no further infusion was possible.

Accordingly, what is needed in the art is a vacuum assist system for preventing vacuum stall when using syringes with peristaltic pumps for infusing a fluid medication into a patient. Additionally, there is a need for a mechanical syringe assist device which is capable of applying a compressive force upon a conventional syringe. What is also needed in the art is an apparatus which can hold the peristaltic pump, the syringe, and a vacuum assist device as a single unit, and which can be attached to a pole or hung from a variety of structures. These needs and more are met and with the present invention, the details of which are discussed more fully hereunder.

BRIEF SUMMARY

In light of the foregoing limitations, the present invention was conceived. According to one aspect of the present invention, a syringe assist system for preventing vacuum stall within an infusion pump is provided. The infusion pump cooperates with a tube assembly which forms a fluid connection between a syringe and a patient, where the syringe is defined by a barrel portion filled with fluid medication, and a syringe plunger with a handle attached thereto. The syringe plunger is configured to be inserted within said barrel portion.

Further, provided is a lock box for housing said infusion pump, and a plunger housed within the lock box which selectively imparts a compressive force upon the syringe and the syringe plunger. Vacuum stall resulting from the infusion pump extracting fluid from the syringe is overcome thereby. The lock box includes a handle mating groove formed thereon for securing the handle of the syringe.

In accordance with another aspect of the present invention, the plunger includes a cocker, a cradle, and a base member. The base member is defined by a pair of opposed lateral sides, a pair of opposed longitudinal sides, a housing attachment side, and an inner surface. The base member further defines a pair of opposed mating members extending along and partially inwardly from the respective longitudinal sides. The cocker and cradle each define a cocker/cradle mating groove for enabling an interlocking sliding relationship between the cocker and the cradle, and collectively define a cocker and cradle structure. The cocker further includes a cocker locking member attached thereto cooperating with a wedge locking member extruded from the lock box to selectively prevent movement thereof along the base member. The cradle further includes a syringe barrel compression member attached thereto for imparting a compressive force upon the syringe. The cocker and the cradle each define an opposed pair of base member mating grooves for cooperating with the mating members. Thus, an interlocking sliding relationship is formed between the cocker and the base member, and between the cradle and the base member.

In accordance with still another aspect of the present invention, the cocker and the cradle are compressively retained by a spring spanning therebetween. The cocker further defines a spring retention member for securing the spring to the cocker; as does the cradle further define a spring retention member for securing the spring to the cradle. The spring has sufficient compressive force to overcome the vacuum stall created within the syringe through withdrawing fluid therefrom. The cocker locking member may also include a flexible cocker locking tab formed thereupon for catching the wedge locking member.

According to yet another aspect of the present invention, a syringe assist plunger for imparting a compressive force upon a syringe cooperating with an infusion pump is provided. The syringe assist plunger includes a cocker having a cocker elongate cradle mating section, a cocker base member mating section disposed thereunder, and a cocker locking member extending generally outwardly from the cradle mating section. The syringe assist plunger also includes a cradle having a cradle elongate cocker mating section and a cradle elongate base member mating section disposed thereunder, and a syringe barrel compression member extending outwardly from said cradle mating section. Still further, the syringe assist plunger includes a base member having a pair of opposed longitudinal sides and a pair of opposed lateral sides, and a pair of cocker/cradle mating members extending along respective ones of opposed longitudinal sides.

In accordance with another aspect of the present invention, the cocker base member mating section is a pair of opposed base mating grooves in a sliding relationship with the pair of cocker/cradle mating member of the base member. Further, the cradle base member mating section is a pair of opposed elongate base mating grooves in a sliding relationship with the pair of cocker/cradle mating member of the base member. The cradle elongate cocker mating section is a pair of opposed cocker mating grooves, and the cocker elongate cradle mating section is a pair of opposed cradle mating members. The pair of opposed cradle mating members is in a sliding relation with the pair of cocker mating grooves. In order to compressively retain the cocker and the cradle, each includes a spring retention member defined by an elongate cylindrical section having an upper end attached to the cocker and cradle, respectively, and a lower end having a tapered cone section.

In order to provide structural rigidity, the cocker locking member is braced by an integral locking member support. The syringe compression member is likewise braced to the cradle by an integral chamfered reinforcement members to limit bending thereof.

According to another aspect of the present invention, a lock box for an infusion pump using syringes is provided. The lock box has a front case defining an infusion pump holding section, a syringe retaining chamber, and a security lock retaining hole. The lock box also has a back case which is in a hinged relationship with the front case and defines an infusion pump holding section, a syringe retaining chamber further defining a syringe handle mating groove and a wedge locking member, and a security lock latching slot. Further, provided is a plunger for compressively retaining the syringe, in which the plunger is attached to the syringe retaining chamber on the back case and cooperates with the edge locking member. Additionally, a security lock is attached to the front case through the security lock retaining hole and cooperates with the security lock latching slot.

Preferably, the lock box is further comprised of a variety of means to attach the same to some other structure. In accordance with one aspect of the present invention in this regard, a loop hardware is attached to the back case for hanging the lock box. Additionally, a post attachment member may be affixed to the back case for attaching the lock box to a post structure.

The lock box may preferably include a variety of openings for ready access to items held therein. In accordance with another aspect of the present invention, the front case further defines an access opening providing user access to function keys on the infusion pump. Furthermore, the back case defines a plurality of access ports for infusion pump outlets.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below in connection with the appended drawings is intended as a description of the presently preferred embodiment of the invention, and is not intended to represent the only form in which the present invention may be constructed or utilized. The description sets forth the functions and the sequence of steps for developing and operating the invention in connection with the illustrated embodiment. It is to be understood, however, that the same or equivalent functions and sequences may be accomplished by different embodiments that are also intended to be encompassed within the spirit and scope of the invention. It is further understood that the use of relational terms such as first and second, top and bottom, and the like are used solely to distinguish one from another entity without necessarily requiring or implying any actual such relationship or order between such entities.

Figure 1:
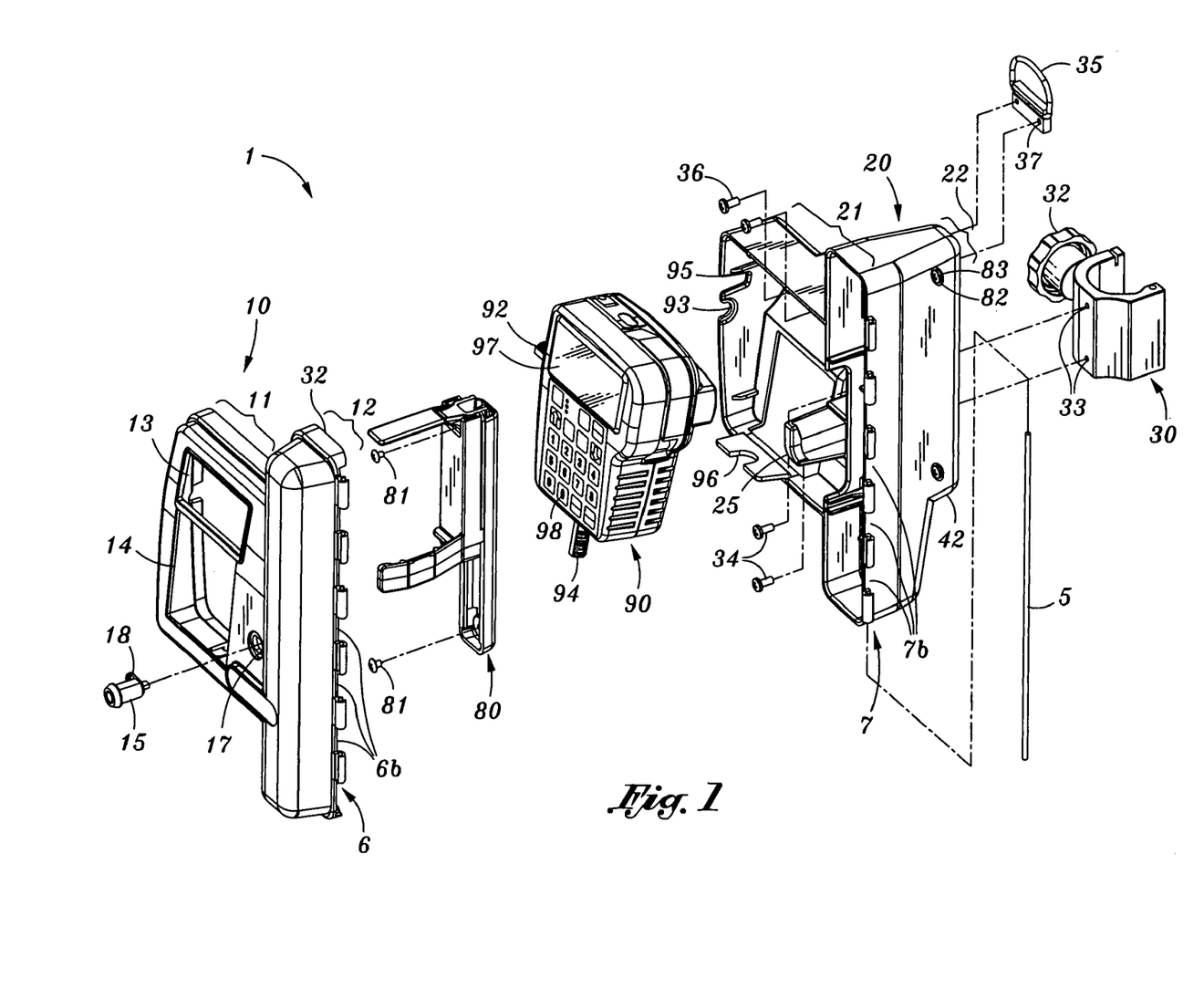
FIG. 1 is an exploded perspective view of a front case, a back case, an infusion pump, and a plunger in accordance with an aspect of the present invention.

With reference to FIG. 1, the present inventive syringe assist device 1 is shown, generally defined by front case 10, back case 20, pump 90, and plunger 80. Pump 90 is preferably a peristaltic pump as disclosed in U.S. Pat. No. 6,164,921 to Moubayed, et al. However, as a person of ordinary skill in the art will recognize, any pump capable of dispensing fluid medication may be substituted, and the present invention is not limited to peristaltic pumps. Pump 90 includes a keypad 98 and a visual display 97, and may also include a first utility cable 92 extending from the lateral side of pump 90, and a second utility cable 94 extending from the bottom side of pump 90, which may provide a variety of inputs such as electrical power and ground, and so forth.

Front case 10 is comprised of a front case pump section 11 that holds and supports pump 90, and a front case syringe section 12 generally defined by front syringe retaining chamber 32, which partially encloses plunger 80 and a syringe (not shown). Front case 10 is further defined by a readout access slot 13 for an unobstructed view of visual display 97, and a keypad access slot 14 for unobstructed access to keypad 98. Front case 10 also defines a security lock retaining hole 17 disposed on front case pump section 11, which is configured to receive a security lock 15. Security lock 15 includes a latch portion 18 which cooperates in a rotational sliding relationship with security lock latching slot 25 on back case 20. This prevents unauthorized access to a syringe (not shown) placed within the enclosure defined by front case 10 and back case 20, as well as any associated components relating to pump 90. Security lock 15 also serves to retain the assembly of front case 10 and back case 20 together so as to collectively form an enclosure of syringe assist device 1 for the components held therein.

Back case 20 is comprised of a case pump section 21 that also holds and supports pump 90, and a back case syringe section 22 generally defined by back syringe retaining chamber 42, which partially encloses plunger 80 and a syringe (not shown). Back case 20 also defines a tube outlet slot 95 which provides an opening for a medication tube to extend from the interior of syringe assist device 1 to the patient. Furthermore, back case 20 defines a first utility cable access slot 93 for providing an opening for first utility cable 92, and a second utility cable access slot 95 for second utility cable 94.

Attached to back case 20 and enclosed within back syringe retaining chamber 42 and front syringe retaining chamber 32 is plunger 80 providing a mechanical assist for a syringe (not shown) during infusion, the details of which are discussed more fully below. Plunger 80 is attached to back case 20 by one or more plunger attaching screws 81.

A number of means may be provided to secure syringe assist device 1 to a variety of structures. One such means is loop hardware 35, which is attached to back case 20 by threading loop hardware attaching screws 36 through loop hardware securing hole 37. This permits syringe assist device 1 to be hung with any type of straps capable of handling the weight of the same, and can be used with conventional mobile IV (intravenous) drip systems utilizing hanging architectures. Another such means is post attachment member 30, which is attached to back case 20 by threading post attachment member attaching screws 34 therethrough, and through retainer holes 33 on post attachment member 30. In operation, syringe assist device 1 may be attached to any vertically elongate structure such as a bedpost or other like structure. In order to accommodate varying widths of such a vertically elongate structure, the insertion depth of post attachment adjustment knob 32 may be varied. Post attachment adjustment knob 32 may be tightened for thinner structures, and loosened for thicker structures.

Back case 20 and front case 10 are in a hinged relationship, which is enabled by the cooperation of back hinge rod retaining members 7, front hinge rod retaining members 6, and hinge rod 5. More particularly, back hinge rod retaining members 7 interface with the gaps 6b formed between each of front hinge rod retaining members 6, and front hinge rod retaining members interface with the gaps 7b formed between each of back hinge rod retaining members 7. All of hinge retaining members 6 and 7 are generally hollow cylinders in which each defines a slot extending along the height of the cylinder. Hinge rod 5 is inserted through hollow center of hinge retaining members 6 and 7, and the alternating slot orientation enables front case 10 and back case 20 to rotate about hinge rod 5 without becoming disconnected therefrom. However, the present invention does not necessarily require such a hinge structure, and may be any one of the numerous hinge mechanisms well known in the art.

Figure 2:
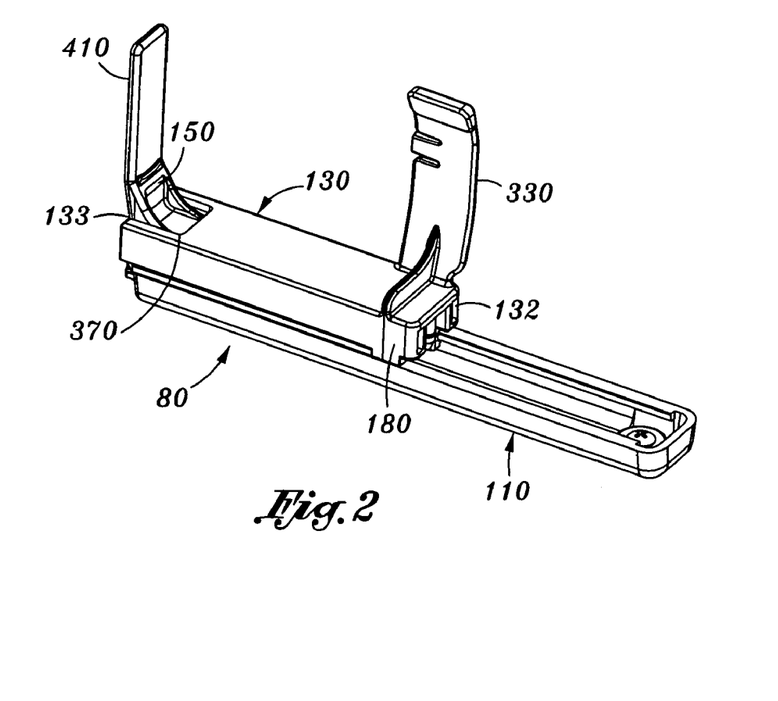
FIG. 2 is a perspective view of a plunger in accordance with an aspect of the present invention.
Figure 3A:
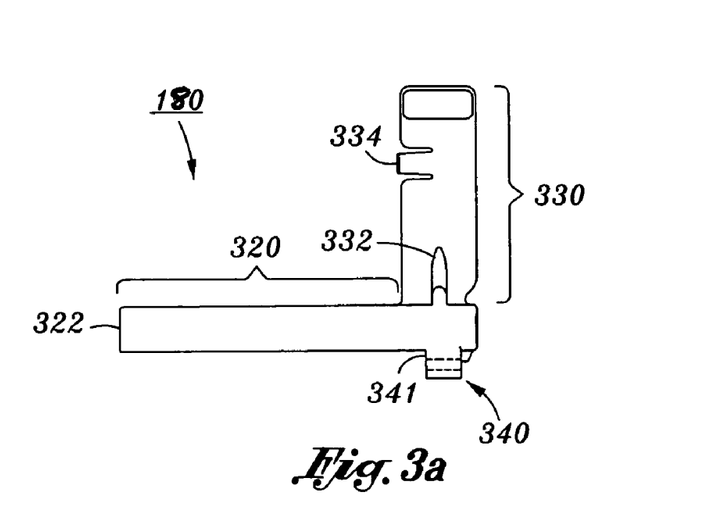
FIG. 3a is a side view of a cocker in accordance with an aspect of the present invention.
Figure 3B:
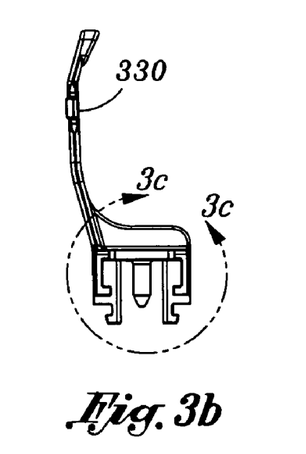
FIG. 3b is a front view of a cocker in accordance with an aspect of the present invention.

With reference to FIG. 2, further details of plunger 80 are shown, which is comprised of cradle 150 in a counter sliding relationship with cocker 180, and the combined structure thereof in a sliding relationship with base member 110. As used herein, the term cocker refers to that feature of the present invention which enables cradle 150 to exert a unidirectional force in cooperation with the other components as discussed hereunder. As shown in FIG. 3a, cocker 180 is defined by a horizontally elongate cradle mating section 320, a vertically elongate cocker locking member 330, and a base member mating section 340 disposed underneath cradle mating section 320 and cocker locking member 330. Cocker locking member 330 is further supported by locking member support 332. Cocker locking member 330 is generally arcuate to accommodate the arcuate structure of the surrounding syringe retaining chamber, and also includes a flexible locking tab 334, the functionality of which is discussed more fully below.

Figure 3C:
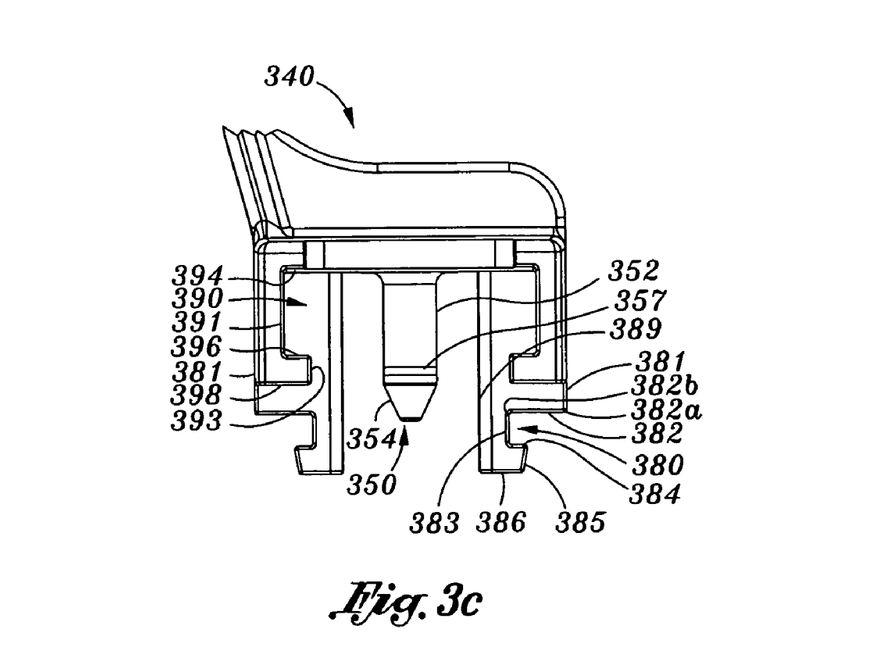
FIG. 3c is a front view of the base member mating section of a cocker in accordance with an aspect of the present invention.

Referring now to FIG. 3c, base member mating section 340 is generally defined by a first cocker side surface 381, a base mating groove 380, and a cradle mating groove 390. Base mating groove 380 is defined by a first cocker bottom surface 382 having an outer end 382a and an inner end 382b, in which outer end 382a forms a perpendicular relationship between first cocker bottom surface 382 and first cocker side surface 381. Additionally, base mating groove 380 is defined by a second cocker side surface 383 in a perpendicular relationship with inner end 382b of first cocker bottom surface 382. Second cocker side surface 383 is also in a perpendicular relationship with first cocker top surface 384. Thus, first cocker bottom surface 382 is in a generally opposed relationship with first cocker top surface 384 separated by a height of second cocker side surface 383. Third cocker side surface 385 is in an angled relationship with first cocker top surface 384, as well as second cocker bottom surface 386. The interior of base member mating section 340 is defined by an interior cocker side surface 389. The aforementioned surfaces have corresponding equivalents on the opposed side of cocker 180. While reference has been made to a variety of surfaces in perpendicular relationship to another surface, the present invention is not limited to such configurations. Any other shape configuration of base mating groove 380 and a corresponding member which are capable of enabling an interlocking, sliding relationship between a cocker and a base is understood to be encompassed by the present invention.

Figure 5A:
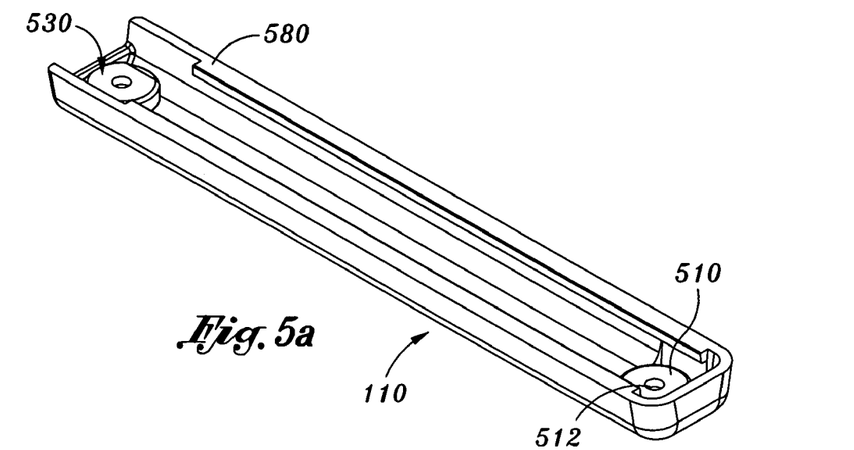
FIG. 5a is a perspective view of a base member in accordance with an aspect of the present invention.
Figure 5B:
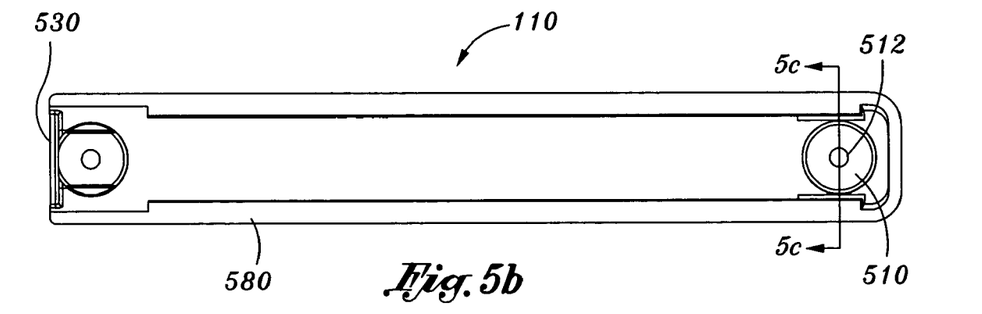
FIG. 5b is a top view of a base member in accordance with an aspect of the present invention.
Figure 5C:
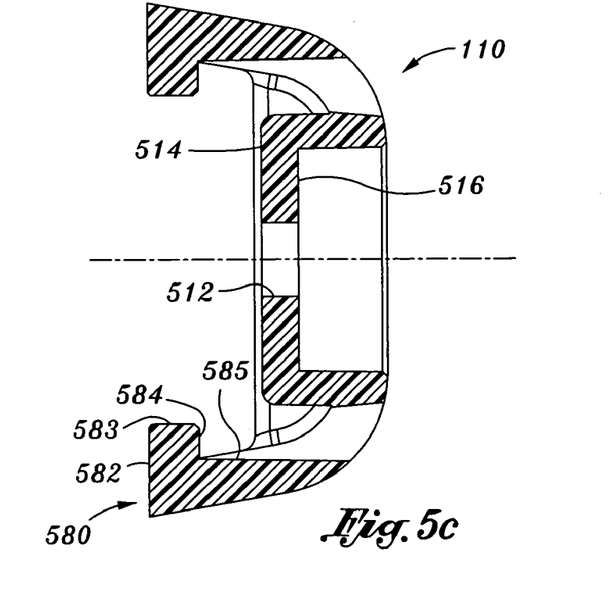
FIG. 5c is a cross sectional view along C-C of FIG. 5b, in accordance with an aspect of the present invention.

Referring now to FIGS. 5c and 3c, base member 110 includes a cocker/cradle mating member 580 which interfaces with base mating groove 380. Cocker/cradle mating member 580 extends from base interior side surface 585, and is further defined by a base top surface 582, a base side surface 583, and a base bottom surface 584. As illustrated by the figures, the aforementioned surfaces have corresponding equivalents on the opposed side of base member 110. Accordingly, first cocker bottom surface 382 is in a sliding relationship with respect to base top surface 582, second cocker side surface 383 is in a sliding relationship with respect to base side surface 583, and first cocker top surface 384 is in a sliding relationship with respect to base bottom surface 584. In order to facilitate an interlocking sliding relationship, the width of first cocker bottom surface 382 is generally equal to the width of base top surface 582, the width of first cocker top surface 384 is generally equal to the width of base bottom surface 584, and the height of second cocker side surface 383 is generally equal to the height of base side surface 583.

Figure 4A:
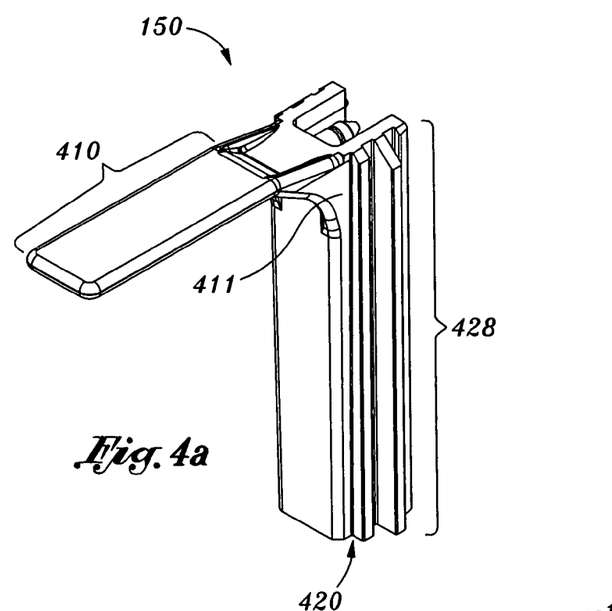
FIG. 4a is a perspective view of a cradle in accordance with an aspect of the present invention.
Figure 4B:
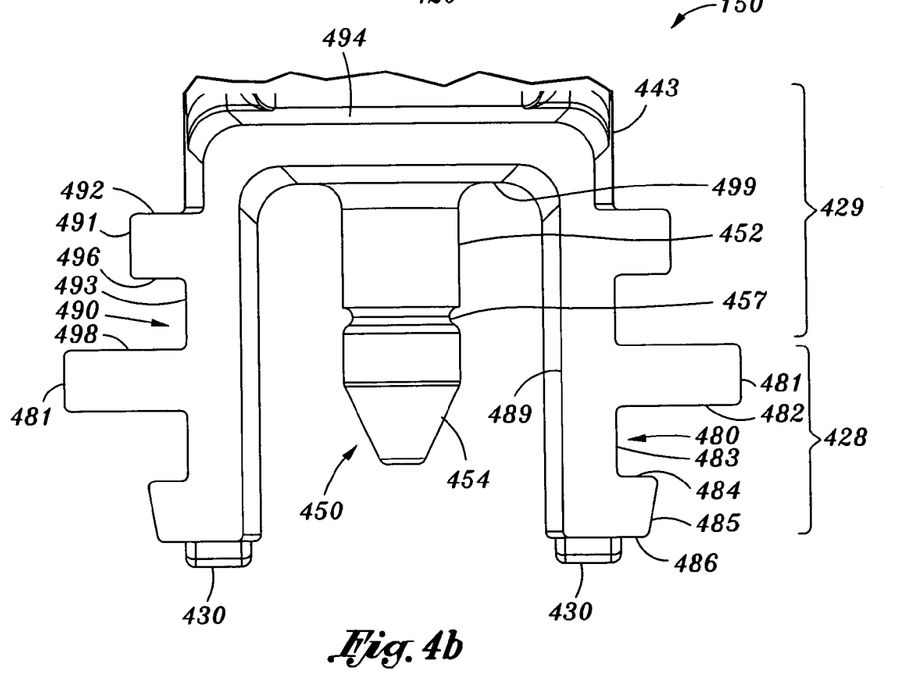
FIG. 4b is a front view of a cradle in accordance with an aspect of the present invention.

In likewise fashion, as illustrated in FIG. 2, cradle 150 interfaces with base member 110 via a base mating groove 480 shown in FIG. 4b. Still referring to FIG. 4b, cradle 150 includes a cocker mating section 429 and a base mating section 428. Base mating section 428 has the aforementioned base mating groove 480, and is generally defined by a first cradle side surface 481, a first cradle bottom surface 482 in a perpendicular relationship with first cradle side surface 481, a second cradle side surface 483 in a perpendicular relationship with first cradle bottom surface 482, a first cradle top surface 484 in a perpendicular relationship with second cradle side surface 483, a third cradle side surface 485 in a generally angled relationship with first cradle top surface 484, and a second cradle bottom surface 486 extending in a generally parallel relationship to first cradle bottom surface 482 and first cradle top surface 484. The interior of cradle 150 is defined by an interior cradle side surface 489 and a cradle interior bottom surface 499. As described in relation to cocker 180 in FIG. 3c, with reference to FIG. 5c and FIG. 4b, base top surface 582 is in a sliding relationship with first cradle bottom surface 482, base side surface 583 is in a sliding relationship with second cradle side surface 483, base bottom surface 584 is in a sliding relationship with first cradle top surface 484, and base interior side surface 585 is in a sliding relationship with third cradle side surface 485. In this regard, cradle 150 also forms an interlocking, sliding relationship with base member 110. Furthermore, the aforementioned surfaces have corresponding equivalents on the opposed side of cradle 150.

With reference to FIGS. 2, 3a, 3c, and 4b, cradle 150 forms an interlocking, sliding relationship to cocker 180. As previously described, cradle 150 includes a cocker mating section 429, which is generally comprised of a cocker making groove 490. Cocker mating groove 490 is generally defined by a first cradle side surface 481, a second cradle top surface 498 in a generally perpendicular relationship thereto, a fourth cradle side surface 493, a third cradle bottom surface 496, a fifth cradle side surface 491, and a third cradle top surface 492. Cocker mating section 429 is further comprised of a sixth cradle side surface 443 and a fourth cradle top surface 494 that defines the upper extremity of cocker mating section 429. Cocker 180 is further defined by a third cocker bottom surface 398 which extends parallely with and is in a sliding relationship to second cradle top surface 498, a fourth cocker side surface 393 likewise extending parellely with and in a sliding relation to fourth cradle side surface 493, a second cocker top surface 396 also extending parallely with and in a sliding relationship with third cradle bottom surface 496, and a fifth cocker side surface 391 extending parallely with and in a sliding relation to fifth cradle side surface 491. It should be noted that the height of fifth cradle side surface 491 is not the equivalent height as fifth cocker side surface 391. Instead, fifth cocker side surface 391 is of a sufficient height to prevent the obstruction of the interlocking sliding relation of cocker 180 and cradle 150. In other words, fifth cocker side surface 391 provides a stand-off means between fourth cradle top surface 494 and fourth cocker bottom surface 394. Additionally, interior cocker side surface 389 is co-planar to interior cradle side surface 489.

As illustrated in FIG. 3c and FIG. 4b, both cocker 180 and cradle 150 include cocker spring retainer 350 and cradle spring retainer 450. Each of cocker spring retainer 350 and cradle spring retainer 450 is individually defined by a cylindrical shaft member 352 and 452, respectively, with a conical tapered section 354 and 454, respectively. Further, there is spring ring retention groove 357 and 457, respectively, formed on cylindrical shaft member 352 and 452, respectively, the utility of which will become apparent below.

The combined cocker/cradle structure 130 upon proper mating between cradle 150 and cocker 180 as shown in FIG. 2 has a proximal end 133 with syringe barrel compression member 410 disposed thereupon and a distal end 132 with cocker locking member 330 disposed thereupon. Furthermore, cocker spring retainer 350 is disposed on the proximal end 133, and cradle spring retainer 450 is disposed on distal end 132. Spring 190 spans across cocker spring retainer 350 and cradle spring retainer 450, thereby imparting a compressive force between proximal end 132 and distal end 133.

Figure 6:
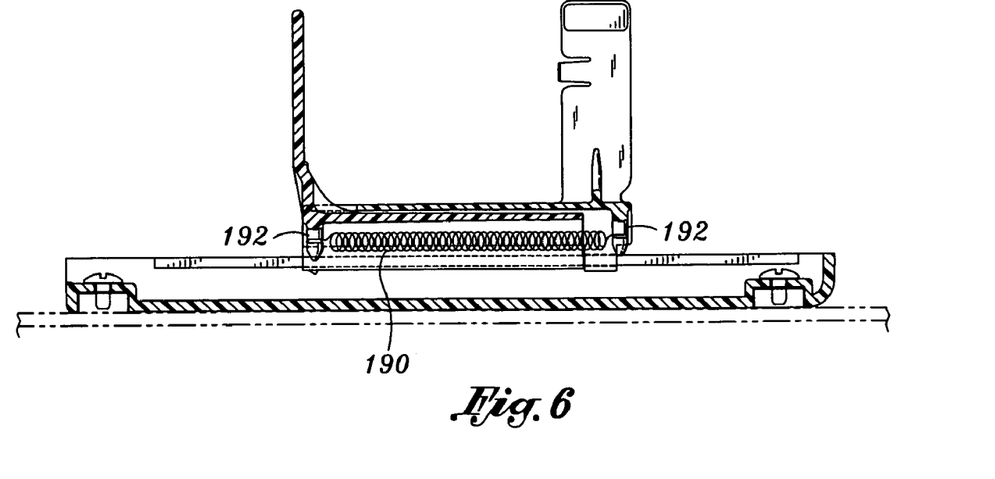
FIG. 6 is a cross sectional side view of the mated cradle/cocker structure with a spring in accordance with an aspect of the present invention.

As illustrated in FIG. 6, spring 190 is a conventional coil spring well known in the art, and includes a pair of spring rings 192 disposed in opposed ends thereof. The diameter of spring rings 192 at its most expanded state is slightly larger than that of cylindrical shaft members 352 and 452, and at its most contracted state is slightly smaller than that of cylindrical shaft member 352 and 452. As will be recognized, spring ring 192 is capable of expansion and contraction due to the malleable characteristics of the metal making up spring 190. The tapering as provided by tapered conical section 354 permits a gradual expansion of spring rings 192 for initial insertion. In order to prevent a constant expanded state of spring rings 192, spring ring retention groove is of a diameter slightly smaller than that of the contracted state of spring rings 192. Thus, the only force imparted upon spring rings 192 is that of the generally lateral compressive force of spring 190 as applied to the extreme ends of the same thereby preventing an omni-directional permanent expansion of spring rings 192. Further, this configuration prevents spring rings 192 from sliding off after extended use.

Reference may now be had to FIG. 2, FIG. 3a, and FIG. 4a, wherein the natural state of the combined cocker/cradle structure 130 is described. Proximal cradle end 420 abuts the distal end 341 of base member mating section 340 on cocker 180, and cradle and base mating section 428 is almost entirely covered by cocker 180. Cradle 150 further includes a syringe barrel compression member 410, and chamfered reinforcement members 411. As will become apparent, syringe barrel compression member 410 exerts a significant amount of force, and chamfered reinforcement members 411 rigidify barrel compression member 410 to minimize bending, thereby increasing the efficiency of the compressive force from spring 190, and preventing breakage. In this regard, in order for cocker 180 to cover base mating section 420 and still accommodate chamfered reinforcement members 411, provided on cocker 180 is a rectangular slot 370 with a length sufficient for cradle proximal end 421 to abut distal end 341 of base member mating section 340 without interfering with the interlocking sliding relationship of cradle 150 and cocker 180.

As a person of ordinary skill in the art will recognize, the above described structure enables cocker 180 and cradle 150 to move about base member 110 in a variety of ways. The combined cocker/cradle structure 130 can slide along base member 110, and cocker 180 can slide along base member 110 independently (subject to the compressive forces of spring 190) of cradle 150. Additionally, cradle 150 can slide along base member 110 independently (again, subject to the compressive forces of spring 190) of cocker 180. In order to prevent casual removal of either cradle 150 or combined cradle/cocker structure 130 inadvertently, FIG. 4b illustrates that cradle 150 is provided with a slide stop 430 on each opposed side of the same, and extends downwards from second bottom surface 486. Slide stop 430 engages base stop 530 as shown in FIGS. 5a and 5b. With sufficient applied force, the frictional forces between slide stop 430 and base stop 530 is overcome, permitting removal of cradle 150, and cocker 180 from base member 110. While in operation, however, it is understood that no such removal need occur, nor should it occur.

Referring back now to FIG. 1, plunger 80 (the combined structure of base member 110, cocker 180 and cradle 150) is secured to back case 20, as mentioned above, via plunger attachment screws 81. Still referring to FIG. 1, and now additionally to FIGS. 5b and 5c, base member 110 includes a back case washer mating extrusion 510, which is generally cylindrical and defines a plunger attachment screw hole 512. Furthermore, back case washer mating extrusion 510 is defined by outer cylinder portion 514 and an inner cylinder portion 516. Back case extrusion 82 is configured to fit within the confines of inner cylinder portion 516. Embedded within back case extrusion 82 is a threaded nut 83, which cooperates with plunger attaching screw 81 to secure plunger 80 to back case 20.

Figure 7:
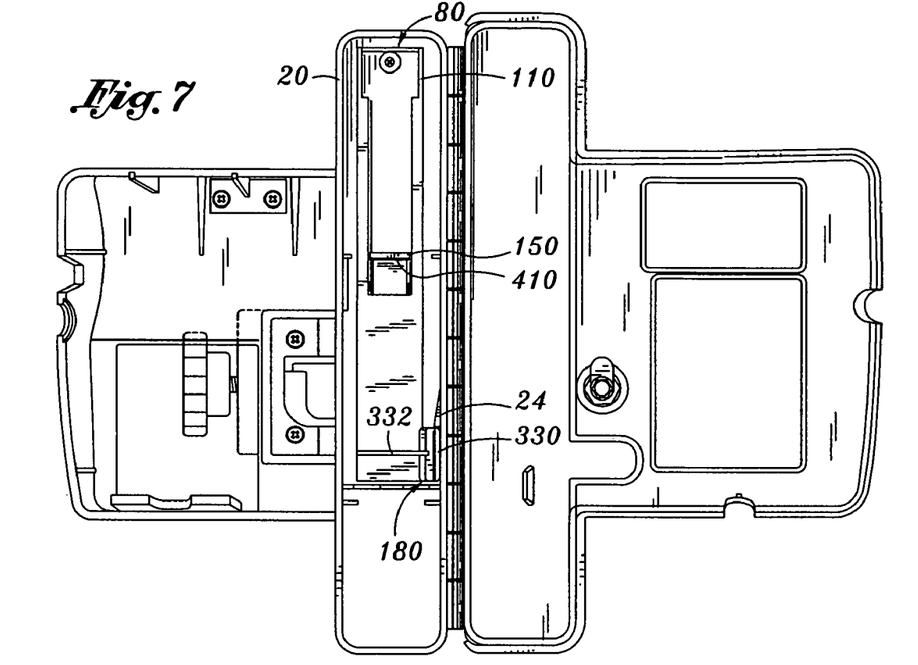
FIG. 7 is a top view of a syringe assist device with a plunger in a locked configuration in accordance with an aspect of the present invention.

With reference to FIG. 7, plunger 80 is shown attached to back case 20, and is in a locked state. Back case 20 additionally defines a wedge type locking member 24 extruded from the same. As shown in FIG. 3a, cocker locking member 330 includes a cocker locking tab 334 which cooperates with wedge type locking member 24. In this way, cocker 150 is locked into position and any movement thereof along base member 110 is prevented. When it is desired for cocker 150 to be unlocked and freely move about base member 110, the flexible characteristics of a cocker locking tab 334 allows effortless disengagement. In order to impart such a flexible characteristic, slots are cut into cocker locking member 330 at the corresponding height of wedge type locking member 24. While in its locked position, it is desirous to maintain that position indefinitely; accordingly, locking member support 332 provides structural rigidity to cocker locking member 330 and prevents the compressive force imparted thereon from bending and disengaging the same from wedge type locking member 24. As will be understood, in its locked state, only cradle 150 is capable of moving about base member 110. Further, as a person having ordinary skill in the art will recognize, in its locked configuration the compressive force provided by spring 190 shown in FIG. 6 is exerted almost entirely through syringe barrel compression member 410 in a downward direction relative to the orientation of FIG. 7.

Figure 8:
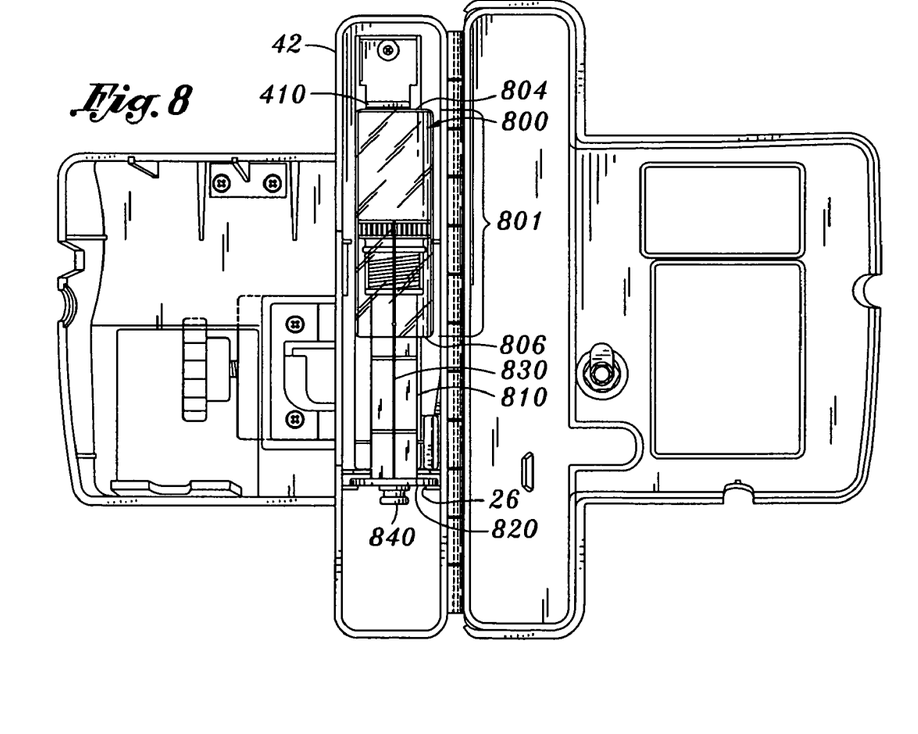
FIG. 8 is top view of a syringe assist device with a plunger providing vacuum assist to a syringe in accordance with an aspect of the present invention.

Next, referring to FIG. 8, a conventional syringe 800 is shown, comprising a barrel portion 801 with distal end 804 and proximal end 806. Additionally, syringe 800 includes a syringe plunger 810, a handle 820 attached thereon, and a needle 830 extending from the interior of barrel portion 801 to tube attachment member 840. As a person having ordinary skill in the art will readily recognize, fluid may be conventionally extracted from barrel portion 801 by depressing syringe plunger 810 further into barrel portion 801, thereby forcing the fluid through need 830 and out of barrel portion 801.

Syringe 800 is secured within back syringe retaining chamber 42 by handle mating groove 26 and syringe barrel compression member 410. Handle mating groove 26 cooperates with handle 820, and distal end 804 of syringe 800 abuts syringe barrel compression member 410. As will be appreciated, the interior of barrel portion 801 can be filled with any one of well known fluid medication. Still referring to FIG. 8, and additionally to FIG. 1, pump 90 infuses a patient with the medication contained in syringe 800 by suction force. In this regard, a tube attached to tube attachment member 840 passes through pump 90 and to a needle (not shown) which is inserted within the patient's body. Fluid medication passes through an opening on syringe plunger 810 and through needle 830 before reaching the aforementioned tube attachment member 840.

As mentioned above, one of the deficiencies in prior art infusion pump systems was that upon suctioning out medication from syringe 800, the pump could not overcome the vacuum force within syringe barrel 801 imparted on syringe plunger 810, thus leading to a vacuum stall. In other words, as more fluid medication was pumped out of syringe barrel 801, a pressure difference developed between the inside of barrel 801 and the outside of the same, because a lesser volume of fluid medication occupied the same space. The vacuum created thusly required a greater output from the pump to properly extract fluid medication, and eventually reached a point where medication could not be infused. However, by imparting a compressive force against distal end 804 of syringe 800, the suction force of the pump can remain constant and also avoid the problem of vacuum stall. As one of ordinary skill in the art will recognize, as fluid medication is extracted from syringe barrel 801, the vacuum created thereby is reduced and/or eliminated because of the assistance provided by syringe barrel compression member 410 in depressing syringe plunger 810 into barrel portion 801. Essentially, fluid medication is extracted from syringe 801 by the aforementioned conventional means of accomplishing the same, but with the added degree of infusion rate control offered by the use of a pump 90. The position of handle 820 remains constant relative to handle mating groove 26, but plunger 810 penetrates further into syringe barrel 801 as force is applied to distal end 804 by syringe barrel compression member 410.

As will be further understood, the compression strength of spring 190 described with reference to FIG. 6 is within an ideal range sufficient to overcome the above mentioned vacuum stall, but insufficient to overcome the pinching force imparted by the pump fingers within pump 90. In this regard, vacuum stall is avoided without an elevated, largely uncontrolled infusion rate of medication into the patient.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

What is claimed is:

1. A syringe assist system for preventing vacuum stall within an infusion pump cooperating with a tube assembly which forms a fluid connection between a syringe and a patient, said syringe defined by a barrel portion filled with fluid medication and a syringe plunger with a handle attached thereto inserted within said barrel portion, wherein the infusion pump operates to suction the fluid medication from the syringe barrel, comprising:

a lock box for housing said infusion pump;
a plunger housed within said lock box which imparts a compressive force urging the syringe plunger into the syringe barrel to overcome said vacuum stall resulting from said infusion pump suctioning fluid from said syringe barrel;
a handle mating groove formed on an interior wall of said lock box for securing said handle of said syringe relative to said lock box;
wherein said plunger includes a cocker, a cradle, and a base member; and
wherein said cocker further includes a cocker locking member attached thereto cooperating with a wedge locking member extruded from said lock box to selectively prevent movement thereof along said base member.

2. The syringe assist system as set forth in claim 1, wherein said base member is defined by a pair of opposed lateral sides, a pair of opposed longitudinal sides, a housing attachment side, and an inner surface, and said base member further defining a pair of opposed mating members extending along and partially inwardly from said respective longitudinal sides.

3. The syringe assist system as set forth in claim 1, wherein said cocker and said cradle each define a cocker/cradle mating groove for enabling an interlocking sliding relationship between said cocker and said cradle and collectively define a cocker and cradle structure.

4. The syringe assist system as set forth in claim 3, wherein said cocker and said cradle are compressively retained by a spring spanning from said cocker to said cradle.

5. The syringe assist system as set forth in claim 4, wherein said cocker further defines a spring retention member for securing said spring to said cocker.

6. The syringe assist system as set forth in claim 4, wherein said cradle further defines a spring retention member for securing said spring to said cradle.

7. The syringe assist system as set forth in claim 4, wherein said spring has sufficient compressive force to overcome said vacuum stall created within said syringe through withdrawing fluid therefrom.

8. The syringe assist system as set forth in claim 1, wherein said cradle further includes a syringe barrel compression member attached thereto for imparting a compressive force upon said syringe.

9. The syringe assist system as set forth in claim 1, wherein said cocker and said cradle each define an opposed pair of base member mating grooves for cooperating with said mating members and enabling an interlocking sliding relationship between said cocker and said base member, and between said cradle and said base member.

10. The syringe assist system as set forth in claim 1, wherein said cocker locking member further includes a flexible cocker locking tab formed thereupon for catching said wedge locking member.

11. A syringe assist plunger for imparting a compressive force upon a syringe cooperating with an infusion pump, comprising:
a cocker having a cocker elongate cradle mating section, a cocker base member mating section disposed thereunder, and a cocker locking member extending generally outwardly from said cradle mating section;
a cradle having a cradle elongate cocker mating section and a cradle elongate base member mating section disposed thereunder, and a syringe barrel compression member extending outwardly from said cradle mating section; and
a base member having a pair of opposed longitudinal sides and a pair of opposed lateral sides, and a pair of cocker/cradle mating members extending along respective ones of opposed longitudinal sides.

12. The syringe assist plunger as set forth in claim 11, wherein said cocker base member mating section is a pair of opposed base mating grooves in a sliding relationship with said pair of cocker/cradle mating member of said base member.

13. The syringe assist plunger as set forth in claim 11, wherein said cradle base member mating section is a pair of opposed elongate base mating grooves in a sliding relationship with said pair of cocker/cradle mating member of said base member.

14. The syringe assist plunger as set forth in claim 11, wherein said cradle elongate cocker mating section is a pair of opposed cocker mating grooves, and said cocker elongate cradle mating section is a pair of opposed cradle mating members, said pair of opposed cradle mating members in a sliding relation with said pair of cocker mating grooves.

15. The syringe assist plunger as set forth in claim 11, wherein said cocker includes a spring retention member defined by an elongate cylindrical section having an upper end attached to said cocker, and a lower end having a tapered cone section.

16. The syringe assist plunger as set forth in claim 11, wherein said cradle includes a spring retention member defined by an elongate cylindrical section having an upper end attached to said cradle, and a lower end having a tapered cone section.

17. The syringe assist plunger as set forth in claim 11, wherein said cocker locking member is braced by an integral locking member support to limit the twisting thereof.

18. The syringe assist plunger as set forth in claim 11, wherein said syringe compression member is braced to said cradle by an integral chamfered reinforcement members to limit bending thereof.

* * * * *